United States Patent [19]

Horowitz

[11] Patent Number: 4,754,745
[45] Date of Patent: Jul. 5, 1988

[54] CONFORMABLE SHEET MATERIAL FOR USE IN BRACHYTHERAPY

[76] Inventor: Bruce S. Horowitz, 33822 Yorkridge, Farmington Hills, Mich. 48018

[21] Appl. No.: 882,444

[22] Filed: Jul. 7, 1986

Related U.S. Application Data

[63] Continuation of Ser. No. 673,858, Nov. 21, 1984, abandoned.

[51] Int. Cl.$^4$ ............................................. A61N 5/12
[52] U.S. Cl. .................................................... 128/1.2
[58] Field of Search .................. 128/1.1, 1.2, 335.5
[56] References Cited

U.S. PATENT DOCUMENTS

| | | | |
|---|---|---|---|
| 1,238,872 | 9/1917 | Bell | 128/1.1 |
| 1,317,082 | 9/1919 | Hartenheim | 128/1.1 |
| 1,494,826 | 5/1924 | Viol | 128/1.2 |
| 1,517,861 | 12/1924 | Rosher | 128/1.1 |
| 1,578,945 | 3/1926 | Withers | |
| 2,067,589 | 1/1937 | Antrim | 47/1 |
| 2,153,889 | 4/1938 | Hames | 128/1.1 |
| 2,322,902 | 6/1943 | Wappler | 29/34 |
| 2,517,513 | 8/1950 | Vaernet | 128/272 |
| 2,829,636 | 4/1958 | Henschke | 128/1.2 |
| 3,127,313 | 3/1964 | Glenn | 167/51 |
| 3,351,049 | 11/1967 | Lawrence | 128/1.2 |
| 3,463,158 | 8/1969 | Schmitt et al. | 123/334 R |
| 3,565,869 | 2/1971 | Prospero | 260/78.3 |
| 3,589,356 | 6/1971 | Silverman | 128/1.2 |
| 3,636,956 | 1/1972 | Schneider | 128/335.5 |
| 3,663,685 | 5/1972 | Evans | 424/1 |
| 3,750,653 | 8/1973 | Simon | 128/1.2 |
| 3,867,190 | 2/1975 | Schmitt et al. | 128/335.5 |
| 3,872,856 | 3/1975 | Clayton | 128/1.2 |
| 3,887,699 | 6/1975 | Yolles | 424/19 |
| 3,927,325 | 12/1975 | Hungate et al. | 250/435 |
| 3,948,263 | 4/1976 | Drake, Jr. et al. | 128/260 |
| 3,950,282 | 4/1976 | Gilbert et al. | 260/9 |
| 3,976,071 | 8/1976 | Sadek | 128/260 |
| 3,978,203 | 8/1976 | Wise | 424/22 |
| 4,014,987 | 3/1977 | Heller et al. | 424/15 |
| 4,052,988 | 10/1977 | Doddi et al. | 128/335.5 |
| 4,054,138 | 10/1977 | Bucalo | 128/260 |
| 4,086,914 | 5/1978 | Moore | 128/1.2 |
| 4,096,239 | 6/1978 | Katz et al. | 424/21 |
| 4,167,179 | 9/1979 | Kirsch | 128/1.2 |
| 4,180,064 | 12/1979 | Heller et al. | 128/130 |
| 4,182,750 | 1/1980 | Sullivan et al. | 424/1 |
| 4,218,255 | 8/1980 | Bajpai et al. | 106/45 |
| 4,249,531 | 2/1981 | Heller et al. | 128/260 |
| 4,304,767 | 12/1981 | Heller et al. | 424/78 |
| 4,309,776 | 1/1982 | Berguer | 3/1 |
| 4,322,398 | 3/1982 | Reiner et al. | 424/19 |
| 4,323,055 | 4/1982 | Kubiatowicz | 128/1.2 |
| 4,351,337 | 10/1982 | Sidman | 128/260 |
| 4,402,308 | 9/1983 | Scott | 128/1.2 |
| 4,509,506 | 4/1985 | Windorski et al. | 128/1.2 |
| 4,510,924 | 4/1985 | Gray | 128/1.2 |
| 4,534,760 | 8/1985 | Raible | 604/175 |
| 4,588,395 | 5/1986 | Lemelson | 604/59 |

FOREIGN PATENT DOCUMENTS

| | | |
|---|---|---|
| 30822 | 6/1981 | European Pat. Off. |
| 64860 | 11/1982 | European Pat. Off. |
| 2240746 | 3/1975 | France |
| 24693 | of 1907 | United Kingdom ............... 128/1.1 |
| 704628 | 2/1954 | United Kingdom ............... 128/1.2 |

OTHER PUBLICATIONS

"Sterilization of $^{125}$I Seeds . . . Implantation", by Martinez et al., Int. J. Radiation Onc. Biol. Phys., vol. 5, #3, pp. 411–413.

"Radio Tags Bar Sponges in Patients", The Evening Star, Washington, D.C., Jul. 22, 1964.

"A Non-Looping . . . the Tongue", by Vikram et al., Int. J. Rad. Onc. Biol. Phys., vol. 7, #3, Mar. 1981, pp. 419–422.

M. Rotman et al., "Intracavitary Applicator in Relation to Complications of Pelvic Radiation", Int. J. Radiation Oncology Biol. Phys., vol. 4, pp. 951–956 (1978).

Blackshear, "Systems", Scientific American, pp. 66 et seq., Dec. 1979.

Primary Examiner—Edward M. Coven
Assistant Examiner—David Shay
Attorney, Agent, or Firm—Robert C. Kain, Jr.

[57] ABSTRACT

A delivery system for brachytherapy comprising a conformable sheet of material which is absorbable in living tissue and a plurality of radioactive seeds in a predetermined array within the sheet. In one form, the sheet is a continuous flexible film in which the seeds are positioned in a predetermined array and which film can be sutured or stapled in place on the surface of a tumor area.

6 Claims, 3 Drawing Sheets

CONFORMABLE SHEET MATERIAL FOR USE IN BRACHYTHERAPY

This application is a continuation of application Ser. No. 673,858, filed Nov. 21, 1984, now abandoned.

This invention relates to brachytherapy and particularly a delivery system for delivering radioactive sources for use in brachytherapy.

BACKGROUND AND SUMMARY OF THE INVENTION

Interstitial radiation therapy, a form of brachytherapy, has been performed since the beginning of the 20th Century. Radium was developed by Madam Curie and Alexander Graham Bell proposed the use of radium in tumors. Subsequently, metal needles were developed in which a radium isotope was encapsulated for insertion in close proximity or into tumors. Where the tumor was deep seated, an operation was necessary to provide access to the tumor. Such therapy had serious problems and disadvantages. The high energy of the radium isotope required a great deal of shielding and subjected the personnel to harmful exposure. In addition, the needles tended to break as they aged resulting in the release of the radioactive contents. Since the radium isotopes had a half-life of about 1600 years, they produced an extreme contamination hazard.

Thus, efforts have been made to develop more effective brachytherapy which is safer and more convenient to use. This has resulted in the development of radioactive materials that have lower energies and thus require less shielding and have shorter half-lives to reduce the risk of contamination. Thus, permanent seeds of encapsulated radon-222 having an energy level of 0.78 MEV and a half-life of 33.83 days or of encapsulated gold-198 having an energy level of 0.42 MEV and a half-life of 2.7 days have been used. More recently small seeds of iridium-192 having an energy level of 0.30 MEV and a half-life of 74.2 days and iodine-125 having an energy level of 0.028 MEV and a half-life of 60 days have been developed. Such seeds are shown, for example, in U.S. Pat. Nos. 3,351,049 and 4,323,055.

Such iridium and iodine seeds are on the order of 4.5 mm in length and 0.8 mm in diameter and are implanted in the tumor or placed on the surface of the tumor. Both of these sources have lower energies than radium that allow for simpler shielding and less radiation exposure to personnel. With seeds of iodine encapsulated in a material such as titanium, shielding is provided by the surrounding tissue and the seeds can be left in the patient permanently without the need for major precautions.

A further development in brachytherapy has been the development of techniques for handling the seeds. In one technique, hollow metal needles are inserted into the tumor and the seeds are thereafter inserted into the needles while the needles are being retracted to deposit the seeds in the tumor. Such devices are shown in U.S. Pat. No. 4,402,308. The most commonly used instruments are the Henschke and Mick devices. The spacing of the needles is determined by a nomograph developed by Drs. H. M. Kuam and L. L. Anderson of the Department of Medical Physics at Memorial Sloan-Kettering Cancer Center, New York, New York. The use of such devices has distinct disadvantages and problems. The overall length of such devices is over 20 cm and they have significant weight making them difficult to manipulate. Since the implant is performed through an open surgical wound, the needles can only be placed straight in a straight line or at an angle dictated by the relationship of the incision to the tumor. For example, the prostate is directly below the pubic bone with the incision being located cephalad. Since the prostate tends to rise behind the bladder, the preferred direction of the implant should be from a caudal approach, but this is not achievable using the available devices.

Another disadvantage of the above technique is that the seeds are deposited in a track made by the needle. When the needle is withdrawn, there is a tendency for the seeds to migrate in that track resulting in a poor distribution of the seeds. Because the energy levels are low (an exposure constant of 0.0184 for iodine-125 vs. $0.825^2 Rm^2 ci^1 h^1$ for radium), distribution between centers of adjacent seeds should be on the order of 1 cm. Poor distribution of seeds can result in undesirable concentrations of seeds resulting in either an overdosage or underdosage of radiation.

The seed is small because it needs to fit in small bore needles which minimally change or damage tissue. The seed has a high seed surface dose and is difficult to handle because of its small size and can be easily lost and difficult to label. In addition, the technique of implantation of individual seeds is time consuming.

In another technique for treating tumors, seeds are initially placed by hand in a woven or braided absorbable carrier such as a braided suture. The carrier with the seeds laced therein is then secured in place to form a suitable implant. This technique is time consuming and may necessitate handling of the suture as well as having the same problems as to position and retention as the catheters. In order to minimize the radiation to personnel during handling and shipping, the suture with the seeds placed therein is shielded by placing it in a curved metallic tube. See European Patent Application Publication Number 0 064 860, published 17.11.82, Bulletin 82/46.

In another technique that has been developed for treatment of tumors, plastic catheters are sutured on or in the tumor area and seeds placed in the catheters by insertion of a nylon tube carrying the seeds. After the desired treatment period, the nylon tubes are removed. The catheters are difficult to place so as to provide the proper dose distribution. It is also difficult to accurately space the catheters in parallel array over irregular surfaces and to anchor the catheters to the tissue. Irregular spacing can result in radiation overdose or underdose. Where the ends of the catheters are brought to the surface of the skin and sutured in place, there is an incipient source of contamination.

None of these prior art systems allow for the adequate placement of the seeds in the configuration of the tumor treated.

Accordingly, one of the objectives of the present invention are to provide a delivery system which obviates the aforementioned disadvantages and places and holds the seeds in the desired and accurate position to provide the desired radiation dose.

Another object of the present invention is to provide a delivery system that is safe and easy to use and causes a minimum of trauma to tissue.

Yet another object of the present invention is a delivery system that allows for excellent control of the radiation dosage given the tumor.

In accordance with the invention, the delivery system comprises a conformable sheet of material absorbable in living tissue which has a plurality of radioactive seeds dispersed therein in a predetermined array. In one form, the sheet comprises a continuous flexible film having radioactive seeds encapsulated therein and which sheet may be attached to the surface of a tumor.

DESCRIPTION

In accordance with the invention, a delivery system of a conformable sheet material which is absorbable in living tissue is provided in the form of a flexible film for placing on and around tumors. The sheet may be attached adjacent a surface harboring a tumor. Radioactive seeds are positioned in a predetermined array in the sheet in the desired spaced relationships.

Figure 3:
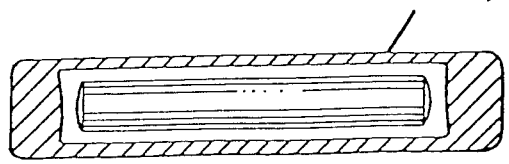
FIG. 3 is an enlarged sectional view of a typical seed utilized in the invention.

The seeds can be of various types having low energy and low half-life such as iodine seeds, known as I-125 seeds, consisting of a welded titanium capsule containing iodine 125 absorbed on a silver rod as shown in FIG. 3. Iridium seeds, designated Ir-192 seeds, can also be used.

The sheet may be made of any of the natural or synthetic absorbable materials. An example of a natural absorbable material that may be used to produce the conformable sheets of the present invention is collagen. Examples of suitable synthetic absorbable materials are the polyester amides derived from glycolic or lactic acids such as the polymers and copolymers of glycolide and lactide, polydioxanone and the like. Such polymeric materials are more fully described in U.S. Pat. Nos. 3,565,869, 3,636,956, 4,052,988 and European Patent Application No. 30822. Specific examples of such polymers are sold by ETHICON, Inc., Somerville, N.J., under the trademarks "VICTYL" and "PDS".

The absorbable material should preferably maintain its integrity for from 1 to 14 days. Preferably the material should be absorbed in living tissue in a period of time of from about 70 to 120 days. It is preferred that as little absorbable material as possible be used in the delivery system of the present invention. The sheet may be a cast sheet, extruded sheet, woven sheet, non-woven sheet or the like.

The radioactive seeds may be dispersed in the sheet in any desired pattern. The seeds may be encapsulated in the sheet; that is, they are totally surrounded by absorbable material so that the sheet is safer and easier to handle.

The sheets of the present invention may be used in accordance with the following technique:

1. The tumor is exposed by a proper surgical technique.

2. The configuration of the tumor is determined.

3. The number and spacing of radioactive sources may be determined by the aforementioned nomograph technique developed by Drs. Kuam and Anderson. This calculation involves utilizing the average dimension and energy of the seeds as variables.

4. A suitable sheet having the desired spacing of seeds is cut to the appropriate size and placed on or around the tumor and preferably sutured or stapled in place.

5. After the sheet is in place, the surgical incision is closed.

6. Dosimetry is monitored using stereo shift orthogonal radiographs and the appropriate computer program.

Figure 1:
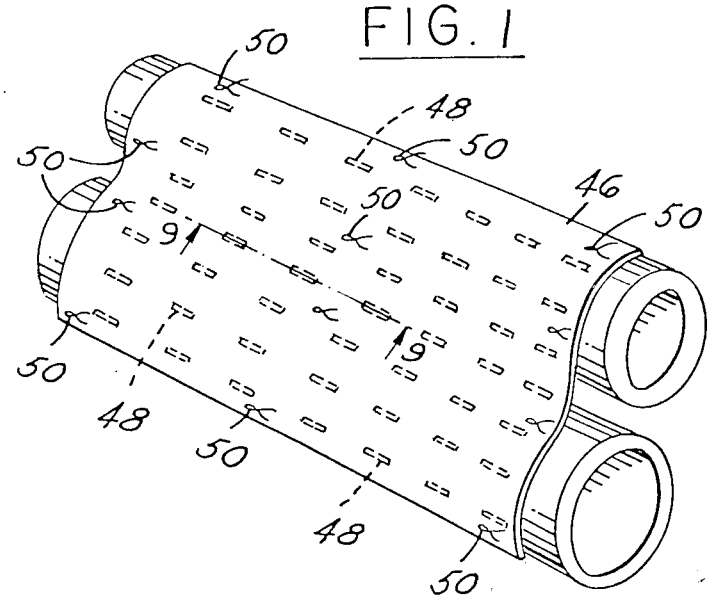
FIG. 1 is a perspective view of a delivery system in the form of a sheet embodying the invention.
Figure 2:
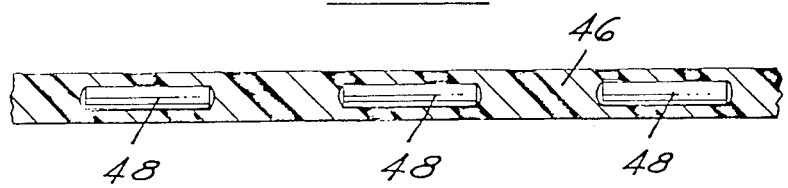
FIG. 2 is an enlarged sectional view taken along the line 2—2 in FIG. 1.

In the form shown in FIGS. 1–3, the delivery system is intended for use on the surface of a tumor or on a tumor bed and comprises a flexible continuous film 46 that can be conformed to the surface of the tumor or tumor bed and attached thereto as by suturing 50. The film is made of an absorbable material and a plurality of seeds 48 are positioned and encapsulated in the film in a predetermined array of spaced seeds. In a typical example, the thickness of the film 1.0 mm.

Figure 4:
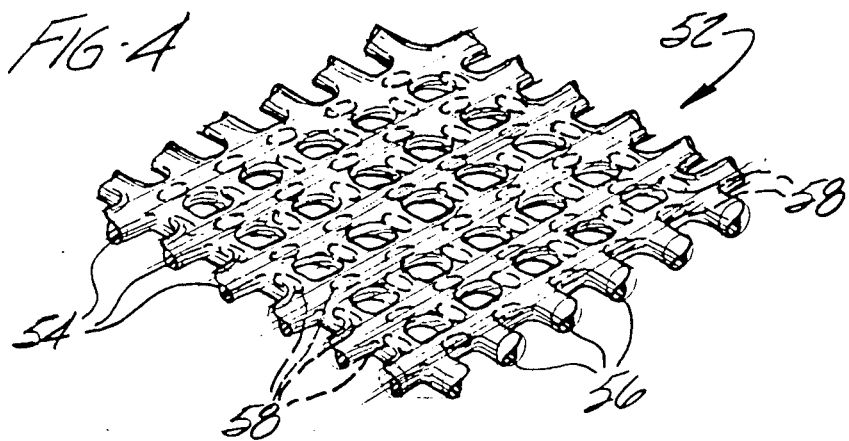
FIG. 4 is a perspective view of another embodiment of the delivery system of the present invention.

In the embodiment depicted in FIG. 4, the conformable sheet delivery system comprises a discontinuous film 52. The film comprises intersecting longitudinal strands 54 and transverse strands 56 which define perforations. In this embodiment radioactive seeds 58 are embedded in the longitudinal strands and the transverse strands at the desired spacing. A suitable spacing is 1 cm between the centers of adjacent seeds in each direction. The sheet may be attached to the tumor by suturing or stapling, as desired.

Figure 5:
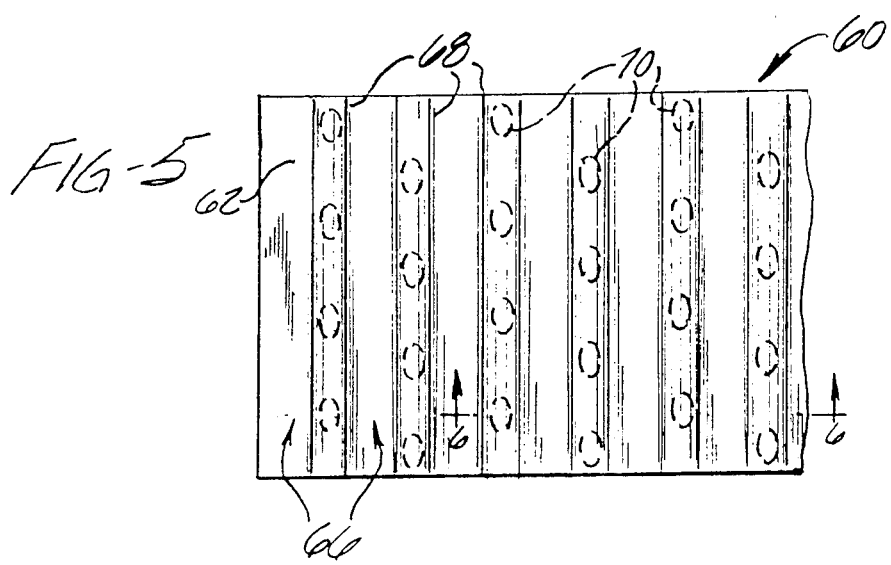
FIG. 5 is a plan view of another embodiment of the delivery system of the present invention.
Figure 6:
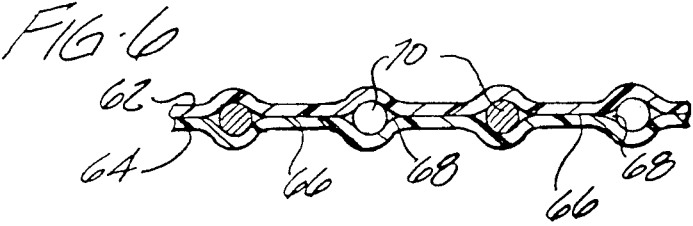
FIG. 6 is a cross-sectional view taken along the line 6—6 in FIG. 5.

Referring to FIGS. 5 and 6, there is shown a laminate 60 of two flexible films 62 and 64 of absorbable polymeric material. The films are secured together at intermittently spaced parallel rows 66. In the areas between the secured rows is a line 68 of radioactive sources 70. Each line comprises a plurality of longitudinally aligned radioactive sources. If desired, the film may also be secured together between adjacent radioactive sources in a line.

The advantages of the improved delivery systems of the present invention are:

1. The sheets may be appropriately configured to the size and shape of the tumor.

2. Fixed linear positioning of seeds to decrease or eliminate "hot" and "cold" spots.

3. If the seed is encapsulated in the absorbable polymer, the normal tissue is spaced away from the seed surface by the thickness of the body of polymer to decrease necrosis from a high local dose.

4. Improved handling and labeling of the seeds that will reduce exposure and error.

5. Increased speed of implant resulting in reduced surgical time and personal exposure.

6. Ease of attachment and localized treatment in critical areas.

What is claimed is:

1. A delivery system for brachytherapy comprising: a conformable continuous sheet made of an organic plastic material which is absorbable in living tissue, said sheet being flexible in all directions such that it can be conformed to a non-planar surface to be treated, and a plurality of spaced radioactive seeds, each seed being non-absorbable, being fixed by, and completely encapsulated within said sheet material to form a predetermined fixed, two dimensional array of discrete, spaced, predetermined distribution of radioactive seeds such that the sheet can be conformed to a surface to be treated and sutured in place.

2. The delivery system set forth in claim 1 wherein said sheet material has elongated passages extending therethrough with the axes of said passages parallel to the plane of the sheet, and said radioactive seeds being embedded in said passages.

3. The delivery system set forth in claim 1 wherein the sheet material comprises a pair of films secured together along spaced parallel rows with radioactive seeds disposed between the films and secured in the areas between said parallel rows.

4. The delivery system set forth in claim 1 wherein the absorbable material is a copolymer of lactide and glycolide.

5. The delivery system set forth in claim 1 wherein the absorbable material is polydioxanone.

6. A method for brachytherapy comprising: exposing a tumor by proper surgical technique, determining the configuration of the tumor, and the desired location of radioactive sources, providing a conformable sheet material which is absorbable in living tissue and has the desired fixed, spaced, discrete, and predetermined distribution of radioactive sources completely embedded in said sheet material, and which is of the appropriate size for the tumor, conforming the sheet to the non-planar surface to be treated, fastening the sheet material in place adjacent the tumor, and closing the surgical incision.

* * * * *